United States Patent

[19]

Kitamura et al.

[11] Patent Number: 6,042,749
[45] Date of Patent: *Mar. 28, 2000

[54] MIXED SOLVENT COMPOSITION

[75] Inventors: Kenroh Kitamura; Michino Ikehata, both of Yokohama; Masaaki Tsuzaki, Ichihara, all of Japan

[73] Assignee: AG Technology Co., Ltd., Yokohama, Japan

[ * ] Notice: This patent is subject to a terminal disclaimer.

[21] Appl. No.: 09/092,309

[22] Filed: Jun. 5, 1998

Related U.S. Application Data

[63] Continuation of application No. 08/578,533, Jan. 18, 1996, Pat. No. 5,827,454.

[30] Foreign Application Priority Data

| May 26, 1994 | [JP] | Japan | 6-113004 |
| May 19, 1994 | [JP] | Japan | 6-105754 |
| Aug. 30, 1994 | [JP] | Japan | 6-205660 |

[51] Int. Cl.$^7$ .............. B01F 1/00; C11D 9/04; C11D 9/00; C11D 15/00; F02B 77/04

[52] U.S. Cl. ............ 252/364; 510/175; 510/179; 510/182; 510/185; 510/245; 510/371; 510/461

[58] Field of Search ............ 252/364; 510/175, 510/179, 182, 185, 245, 371, 461

[56] References Cited

U.S. PATENT DOCUMENTS

| 5,531,916 | 7/1996 | Merchant | 510/412 |
| 5,827,454 | 10/1998 | Kenroh et al. | 252/364 |

*Primary Examiner*—Cynthia Harris
*Assistant Examiner*—Monique T. Cole
*Attorney, Agent, or Firm*—Oblon, Spivak, McClelland, Maier & Neustadt, P.C.

[57] ABSTRACT

A mixed solvent composition comprising dichloropentafluoropropane and at least one component selected from the group consisting of 1,1,1,2,3,4,4,5,5,5-decafluoropentane and perfluorohexane as the essential components, or a mixed solvent composition comprising dichloropentafluoropropane, an alcohol and at least one component selected from the group consisting of 1,1,1,2,3,4,4,5,5,5-decafluoropentane and perfluorohexane.

6 Claims, No Drawings

MIXED SOLVENT COMPOSITION

This application is a Continuation Division Continuation-in-part (CIP) of application Ser. No. 08/578,533, now U.S. Pat. No. 5,827,454 filed on Jan. 18, 1996 which was filed as International Application PCT/JP95/00948 on May 18, 1995.

BACKGROUND OF THE INVENTION

1. Field of the Invention

The present invention relates to mixed solvent compositions used as cleaning agents for electronic components including a printed circuit board and an IC, precision machinery parts, of glass substrates, for example.

Abbreviations and terms used in the present specification are illustrated below.

R113: 1,1,2-trichloro-1,2,2-trifluoroethane
R225; a mixture of one or two or more of dichloropentafluoropropane having the molecular formula $C_3HCl_2F_5$
R225ca: 3,3-dichloro-1,1,1,2,2-pentafluoropropane
R225cb: 1,3-dichloro-1,1,2,2,3-pentafluoropropane
R225mix: a mixture of at least two dichloropentafluoropropane isomers selected from the group consisting of R225ca, R225cb and other dichloropentafluoropropane isomers
R43-10mee: 1,1,1,2,3,4,4,5,5,5-decafluoropentane R51-14M: a mixture of one or two or more of perfluorohexane having the molecular formula $C_6F_{14}$
R51-14: perfluoro (n-hexane)
R51-14my: perfluoro (4-methylpentane)
R51-14mcy: pefluoro (3-methylpentane)
R51-14mix: a mixture of at least two perfluorohexane isomers selected from the group consisting of R51-14, R51-14my, R51-14mcy and other perfluorohexane isomers
Azeotropic mixed solvent composition: a mixed solvent composition, the composition of which does not substantially vary even by repeating distillation-condensation operations
Azeotropic-like mixed solvent composition: a mixed solvent composition, the composition of which varies only within the range of ±2% even by repeating distillation-condensation operations

2. Description of the Background

To remove various oils, greases, or fluxes for example, R113 which is nonflammable, low toxic and excellent in stability, or a mixed solvent composition comprising R113 and a solvent miscible with R113 is widely used. Since R113 has such characteristics that it does not have an adverse effect on a base material such as a metal, a plastic or an elastomer and selectively dissolves various soils, it has been suitable for cleaning various electronic components, precision machinery parts, or components for example, made of a metal, a plastic, or an elastomer for example. Also, U.S. Pat. No. 5,304,322 discloses a cleaning agent for aircrafts, which comprises a $C_4$–$C_8$ perfluorocarbon, a $C_2$–$C_5$ hydrochlorofluorocarbon and a $C_5$–$C_9$ petroleum distillate. In spite of various advantages of conventionally used R113, its production and consumption are regulated, because it has such a long life time in the troposphere by virtue of its chemical stability that it can diffuse to the stratosphere, where it is decomposed by an ultraviolet ray, producing chlorine radicals and the chlorine radicals cause a chain reaction with stratospheric ozone to deplete the ozone layer.

For this reason, alternative solvents to R113, which do not cause depletion of the ozone layer are widely being researched.

An object of the present invention is to provide a novel mixed solvent composition which satisfies the excellent properties of conventional R113 and can be used as an alternative solvent which does not substantially affect the ozone layer.

DISCLOSURE OF INVENTION

The present invention has been made to accomplish the above object, and provides a mixed solvent composition which comprises R225 and at least one component selected from the group consisting of R43-10mee and R51-14M, as the essential components, and a mixed solvent composition which comprises R225, an alcohol and at least one component selected from the group consisting of R43-10mee and R51-14M. In the following description including Examples, "%" means "% by weight".

In the mixed solvent composition comprising R225 and at least one of R43-10mee and R51-14M, as the essential components, the proportion of each of R43-10mee and R51-14M is preferably from 10 to 1,000 parts by weight to 100 parts by weight of R225. More preferable examples include the following azeotoropic or azeotropic-like mixed solvent compositions (1) to (13).

(1) An azeotropic-like mixed solvent composition comprising from 40 to 55% of R43-10mee and from 45 to 60% of R225ca.

(2) An azeotropic mixed solvent composition comprising 48% of R43-10mee and 52% of R225ca.

(3) An azeotropic-like mixed solvent composition comprising from 50 to 70% of R43-10mee and from 30 to 50% of R225cb.

(4) An azeotropic mixed solvent composition comprising 58% of R43-10mee and 42% of R225cb.

(5) An azeotropic-like mixed solvent composition comprising from 10 to 50% of R225mix and from 50 to 90% of R43-10mee.

(6) An azeotropic-like mixed solvent composition comprising from 30 to 75% of R225ca and from 25 to 70% of R51-14mix comprising R51-14 as the main component.

(7) An azeotropic-like mixed solvent composition comprising from 30 to 75% of R225ca and from 25 to 70% of R51-14.

(8) An azeotropic mixed solvent composition comprising 55% of R225ca and 45% of R51-14.

(9) An azeotropic-like mixed solvent composition comprising from 25 to 60% of R225cb and from 40 to 75% of R51-14mix comprising R51-14 as the main component.

(10) An azeotropic-like mixed solvent composition comprising from 25 to 60% of R225cb and from 40 to 75% of R51-14.

(11) An azeotropic mixed solvent composition comprising 45% of R225cb and 55% of R51-14.

(12) An azeotropic-like mixed solvent composition comprising from 25 to 70% of R225mix and from 30 to 75% of R51-14mix comprising R51-14 as the main component.

(13) An azeotropic-like mixed solvent composition comprising from 25 to 70% of R225mix and from 30 to 75% of R51-14.

The present invention further provides a mixed solvent composition comprising R225, an alcohol and at least one component selected from the group consisting of R43-10mee and R51-14M, as the essential components. Preferably, in this composition, the proportion of R43-10mee is from 10 to 1000 parts by weight, the proportion of R51-14M is from 30 to 500 parts by weight and the proportion of an alcohol is from 1 to 100 parts by weight, to 100 parts by weight of R225. More preferable examples include the following azeotrophic or azeotrophic-like mixed solvent compositions (14) to (16).

(14) An azeotropic-like mixed solvent composition comprising from 20 to 50% of R225mix, from 45 to 75% of R51-14M and from 3 to 10% of methanol.

(15) An azeotropic-like mixed solvent composition comprising from 20 to 45% of R225mix, from 47 to 75% of R51-14M and from 3 to 8% of ethanol.

(16) An azeotropic-like mixed solvent composition comprising from 20 to 60% of R225mix, from 38.5 to 75% of R51-14M and from 1.5 to 7% of 2-propanol.

In addition to the above-mentioned methanol, ethanol and 2-propanol, preferable other examples of an alcohol include 1-propanol, 1-buthanol, 2-buthanol, isobuthanol, t-buthanol and the like.

Preferable examples of R225 include R225ca or R225cb respectively alone or a mixture of R225ca and R225cb. The mixture of R225ca and R225cb is preferably a mixture of from 0.01 to 99.99% of R225ca and from 0.01 to 99.99% of R225cb, more preferably a mixture of from 1 to 99% of R225ca and from 1 to 99% of R225cb. The mixture of R225ca and R225cb exhibits azeotropic-like action in a wide composition range. A preferable example of R225mix include a mixture of R225ca and R225cb.

R51-14M is preferably R51-14, R51-14my or R51-14mcy respectively alone or a mixture of at least one of these compounds. When R51-14M is a mixture, such a mixture should preferably comprise R51-14 as the main component. A preferable mixture example of R51-14M is a mixture comprising from 65 to 77% of R51-14, from 16 to 26% of R51-14my and from 2 to 12% of R51-14mcy, more preferably a mixture comprising from 70 to 75% of R51-14, from 18 to 22% of R51-14my and from 5 to 10% of R51-14mcy.

In order to improve mainly a dissolving property, the mixed solvent composition of the present invention may contain one or two or more compounds selected from the following compounds in an amount of from 0.1 to 50%, preferably from 0.1 to 30%, more preferably from 0.1 to 20%:

hydrocarbons such as n-pentane, 2-methylbutane, 2,2-dimethylpropane, n-hexane, 3-methylpentane, 2,2-dimethylbutane, 2,3-dimethylbutane, n-heptane, 2-methylhexane, 3-methylhexane, 2,3-dimethylpentane, 2,4-dimethylpentane, n-octane, 2,2,3-trimethylpentane, 2,2,4-trimethylpentane, cyclopentane, cyclohexane, methylcyclohexane and ethylcyclohexane;

chlorinated hydrocarbons such as dichloromethane cis-1,2-dichloroethylene, trans-1,2-dichloroethylene, trichloroethylene and tetrachloroethylene;

ketones such as acetone, methyl ethyl ketone, methyl butyl ketone and methyl isobutyl ketone;

ethers such as diethyl ether, methyl cellosolve, tetrahydrofuran and 1,4-dioxane;

chlorofluorohydrocarbons such as 2,2-dichloro-1,1,1-trifluoroethane and 1,1-dichloro1-fluoroethane; and esters such as methyl acetate, ethyl acetate, propyl acetate and butyl acetate.

In order to improve mainly a stability, the mixed solvent composition of the present invention may contain one or two or more compounds selected from the following compounds in an amount of from 0.001 to 10%, preferably from 0.001 to 5%:

nitro compounds such as nitromethane, nitroethane, nitropropane and nitrobenzene;

amines such as diethylamine, triethylamine, i-propylamine, n-butylamine and i-butylamine;

phenols such as phenol, o-cresol, m-cresol, p-cresol, thymol, p-t-butylphenol, t-butylcatechol, catechol, isoeugenol, o-methoxyphenol, bisphenol A, isoamyl salicylate, benzyl salicylate, methyl salicylate and 2,6-di-t-butyl-p-cresol; and triazoles such as 2-(2'-hydroxy-5'-methyl-phenyl) benzotriazole, 2-(2'-hydroxy-3'-t-buthyl-5'-methylphenyl)-5-chlorobenzotriazole, 1,2,3-benzotriazole and 1-[(N,N-bis-2-ethylhexyl) aminomethyl]benzotriazole.

The mixed solvent composition of the present invention has a dissolving power at the same degree as a conventional R113 type solvent, and can be used suitably in various ways. Specifically, it is used as a paint solvent, an extractant, or a cleaning agent for removing grease, oil, wax, ink or the like. Also, it is used as a cleaning agent or a dust-removing agent for glass, ceramic, plastic, elastomer, rubber, metal or other various articles. More specifically, it is used suitably as a cleaning agent or a dust-removing agent for ICs, electric devices, precision machines, optical lenses or the like.

As a cleaning method, various methods including manual wiping, immersing, spraying, vibrating, supersonic cleaning, vapor degreasing or a combination of these methods, may be used.

The mixed solvent composition of the present invention provides the excellent properties of conventional R113 and also provides an advantage that it does not substantially affect the ozone layer.

BEST MODE FOR CARRYING OUT THE INVENTION

The present invention is further illustrated by the following Examples.

Evaluation was conducted by the following three methods.

(1) A test coupon (25 mm×30 mm×2 mm) made of SUS-304 was dipped in a machine oil (CQ-30, manufactured by Nippon Petrochemicals Co., Ltd.) and then immersed in the mixed solvent compositions of the present invention as identified in Tables for 5 minutes. Thereafter, the degree of removal of the machine oil was evaluated. The results are shown with evaluation standards for the degree of removal A such that ⊙: excellently removed, Δ: slightly remained and X: substantially remained.

(2) Flux (speedy flux AGF-J-I: manufactured by Asahi Kagaku Kenkyusho) was coated on the entire surface of a printed circuit board (50 mm×100 mm×1.6 mm) made of epoxy-glass, and soldering was carried out at a soldering temperature of 260° C. by means of a wave soldering machine. Then, defluxing was carried out by immersing it in the compositions of the present invention as identified in Tables for 3 minutes, and the degree of removal of the flux was evaluated. The results are shown with evaluation standards for the degree of removal B such that ⊙: excellently removed, Δ: slightly remained and X: substantially remained.

(3) A glass plate of 30 mm×18 mm×5 mm in size was dipped in pure water and then immersed in the compositions of the present invention shown in Tables for 20 seconds to be dewatered. The glass plate was taken out and immersed in anhydrous methanol, and the degree of removal of deposited water was evaluated from the increase of water in the methanol. The results are shown with evaluation standards for the degree of removal C such that ⊚: excellently removed, Δ: slightly remained and X: substantially remained.

EXAMPLE 1

1,000 g of a mixed solvent composition consisting of 48% of R43-10mee (b.p. 53.6° C.) and 52% of R225ca (b.p. 51.1° C.) was charged into a distillation flask, and the flask was connected to a distillation column having a number of theoretical plates of 5. Then, the composition was heated and refluxed for 2 hours. After the composition reached equilibrium, the fraction was periodically collected and analyzed by gas chromatography. The results are shown in Table 1.

TABLE 1

| Portion of fraction | Composition (%) | |
|---|---|---|
| collected (%) | R43-10mee | R225ca |
| 20 | 48.0 | 52.0 |
| 40 | 48.0 | 52.0 |
| 60 | 48.0 | 52.0 |

EXAMPLE 2

20 kg of mixed solvent composition consisting of 55% of R43-10mee and 45% of R225ca was charged into a small degreaser with one-sump, and the degreaser was operated for 6 hours per day for 3 days. Samples were periodically taken from the cleaning sump and the water separator and analyzed by gas chromatography. The results are shown in Table 2.

TABLE 2

| | Composition (%) | | | |
|---|---|---|---|---|
| | Cleaning sump | | Water separator | |
| Time | R43-10mee | R225ca | R43-10mee | R225ca |
| After 6 hours | 55.0 | 45.0 | 55.0 | 45.0 |
| After 12 hours | 55.1 | 44.9 | 55.0 | 45.0 |
| After 18 hours | 55.1 | 44.9 | 54.9 | 45.1 |

EXAMPLE 3

The same procedure as in Example 2 was repeated, except that 20 kg of a mixed solvent composition consisting of 40% of R43-10mee and 60% of R225ca was used as a mixed solvent composition. The results are shown in Table 3.

TABLE 3

| | Composition (%) | | | |
|---|---|---|---|---|
| | Cleaning sump | | Water separator | |
| Time | R43-10mee | R225ca | R43-10mee | R225ca |
| After 6 hours | 40.0 | 60.0 | 40.0 | 60.0 |
| After 12 hours | 39.9 | 60.1 | 40.1 | 59.9 |
| After 18 hours | 39.9 | 60.1 | 40.1 | 59.9 |

EXAMPLE 4

The same procedure as in Example 1 was repeated, except that 1,000 g of a mixed solvent composition consisting of 58% of R43-10mee and 42% of R225cb (b.p. used as a mixed solvent composition. The shown in Table 4.

TABLE 4

| Portion of fraction | Composition (%) | |
|---|---|---|
| collected (%) | R43-10mee | R225cb |
| 20 | 58.0 | 42.0 |
| 40 | 58.0 | 42.0 |
| 60 | 58.0 | 42.0 |

EXAMPLE 5

The same procedure as in Example 2 was repeated, except that 20 kg of a mixed solvent composition consisting of 70% of R43-10mee and 30% of R225cb was used as a mixed solvent composition. The results are shown in Table 5.

TABLE 5

| | Composition (%) | | | |
|---|---|---|---|---|
| | Cleaning sump | | Water separator | |
| Time | R43-10mee | R225cb | R43-10mee | R225cb |
| After 6 hours | 70.0 | 30.0 | 70.0 | 30.0 |
| After 12 hours | 70.1 | 29.9 | 70.0 | 30.0 |
| After 18 hours | 70.1 | 29.9 | 69.9 | 30.1 |

EXAMPLE 6

The same procedure as in Example 2 was repeated, except that 20 kg of a mixed solvent composition consisting of 50% of R43-10mee and 50% of R225cb was used as a mixed solvent composition. The results are shown in Table 6.

TABLE 6

| | Composition (%) | | | |
|---|---|---|---|---|
| | Cleaning sump | | Water separator | |
| Time | R43-10mee | R225cb | R43-10mee | R225cb |
| After 6 hours | 50.0 | 50.0 | 50.0 | 50.0 |
| After 12 hours | 49.9 | 50.1 | 50.1 | 49.9 |
| After 18 hours | 49.9 | 50.1 | 50.1 | 49.9 |

EXAMPLE 7

The same procedure as in Example 2 was repeated, except that 20 kg of a mixed solvent composition consisting of 90% of R43-10mee and 10% of R225mix (R225ca/R225cb=45%/55% mixture) was used as a mixed solvent composition. The results are shown in Table 7.

TABLE 7

| | Composition (%) | | | |
|---|---|---|---|---|
| | Cleaning sump | | Water separator | |
| Time | R43-10mee | R225mix | R43-10mee | R225mix |
| After 6 hours | 90.0 | 10.0 | 90.0 | 10.0 |
| After 12 hours | 90.1 | 9.9 | 89.9 | 10.1 |
| After 18 hours | 90.1 | 9.9 | 89.9 | 10.1 |

EXAMPLE 8

The same procedure as in Example 2 was repeated, except that a mixed solvent composition consisting of 50% R43-

10mee and 50% of R225mix (R225ca/R225cb=45%/55% mixture) was used as a mixed solvent composition. The results are shown in Table 8.

TABLE 8

| Time | Composition (%) | | | |
|---|---|---|---|---|
| | Cleaning sump | | Water separator | |
| | R43-10mee | R225mix | R43-10mee | R225mix |
| After 6 hours | 50.0 | 50.0 | 50.0 | 50.0 |
| After 12 hours | 50.0 | 50.0 | 50.0 | 50.0 |
| After 18 hours | 49.9 | 50.1 | 50.1 | 49.9 |

EXAMPLES 9 to 16

By using the mixed solvent compositions shown in Table 9, a machine oil cleaning test (A) was carried out.

TABLE 9

| No | Solvent composition | % | Degree of removal A |
|---|---|---|---|
| 9 | R43-10mee | 55 | ◎ |
|   | R225ca | 45 | |
| 10 | R43-10mee | 48 | ◎ |
|   | R225ca | 52 | |
| 11 | R43-10mee | 40 | ◎ |
|   | R225ca | 60 | |
| 12 | R43-10mee | 70 | ◎ |
|   | R225cb | 30 | |
| 13 | R43-10mee | 58 | ◎ |
|   | R225cb | 42 | |
| 14 | R43-10mee | 50 | ◎ |
|   | R225cb | 50 | |
| 15 | R43-10mee | 90 | ◎ |
|   | R225ca | 4 | |
|   | R225cb | 6 | |
| 16 | R43-10mee | 50 | ◎ |
|   | R225ca | 10 | |
|   | R225cb | 40 | |

EXAMPLES 17 to 24

By using the mixed solvent compositions shown in Tables 10 and 11, a defluxing test (B) was carried out.

TABLE 10

| No | Solvent composition | % | Degree of removal B |
|---|---|---|---|
| 17 | R43-10mee | 50 | ◎ |
|   | R225ca | 40 | |
|   | 2-propanol | 10 | |
| 18 | R43-10mee | 45 | ◎ |
|   | R225ca | 50 | |
|   | methanol | 5 | |
| 19 | R43-10mee | 36 | ◎ |
|   | R225ca | 56 | |
|   | ethanol | 8 | |
| 20 | R43-10mee | 60 | ◎ |
|   | R225cb | 30 | |
|   | methanol | 10 | |

TABLE 11

| No | Solvent composition | % | Degree of removal B |
|---|---|---|---|
| 21 | R43-10mee | 55 | ◎ |
|   | R225cb | 40 | |
|   | 2-propanol | 5 | |

TABLE 11-continued

| No | Solvent composition | % | Degree of removal B |
|---|---|---|---|
| 22 | R43-10mee | 47 | ◎ |
|   | R225cb | 47 | |
|   | ethanol | 6 | |
| 23 | R43-10mee | 80 | ◎ |
|   | R225ca | 4 | |
|   | R225cb | 6 | |
|   | methanol | 10 | |
| 24 | R43-10mee | 50 | ◎ |
|   | R225ca | 20 | |
|   | R225cb | 25 | |
|   | 2-propanol | 5 | |

EXAMPLES 25 to 32

By using the mixed solvent compositions shown in Tables 12 and 13, a test (C) for removing deposited water was carried out.

TABLE 12

| No | Solvent composition | % | Degree of removal C |
|---|---|---|---|
| 25 | R43-10mee | 53 | ◎ |
|   | R225ca | 42 | |
|   | 2-propanol | 5 | |
| 26 | R43-10mee | 40 | ◎ |
|   | R225ca | 50 | |
|   | ethanol | 10 | |
| 27 | R43-10mee | 35 | ◎ |
|   | R225ca | 50 | |
|   | methanol | 15 | |
| 28 | R43-10mee | 62 | ◎ |
|   | R225cb | 33 | |
|   | methanol | 5 | |

TABLE 13

| No | Solvent composition | % | Degree of removal C |
|---|---|---|---|
| 29 | R43-10mee | 55 | ◎ |
|   | R225cb | 35 | |
|   | ethanol | 10 | |
| 30 | R43-10mee | 46 | ◎ |
|   | R225cb | 46 | |
|   | 2-propanol | 8 | |
| 31 | R43-10mee | 85 | ◎ |
|   | R225ca | 5 | |
|   | R225cb | 2 | |
|   | ethanol | 8 | |
| 32 | R43-10mee | 45 | ◎ |
|   | R225ca | 10 | |
|   | R225cb | 35 | |
|   | methanol | 10 | |

EXAMPLE 33

250 cc of a mixed solvent composition of R225ca (b.p. 51.1° C.) and R51-14 (b.p. 56° C.) in such a ratio as shown 14 was charged into an Othmer type gas-liquid equilibrium distillation apparatus, and was heated. After the composition reached equilibrium, samples were taken from the gas phase and the liquid phase and were analyzed by gas chromatography. The results are shown in Table 14. The azeotropic composition was R225ca/R51-14=55.0%/45.0%.

TABLE 14

| Example 33: Gas phase composition (%) | | Example 33: Liquid phase composition (%) | |
|---|---|---|---|
| R225ca | R51-14 | R225ca | R51-14 |
| 90.0 | 10.0 | 94.0 | 6.0 |
| 75.0 | 25.0 | 79.0 | 21.0 |
| 55.0 | 45.0 | 55.0 | 45.0 |
| 43.0 | 57.0 | 40.0 | 60.0 |
| 30.0 | 70.0 | 25.0 | 75.0 |
| 14.0 | 86.0 | 10.0 | 90.0 |

EXAMPLE 34

1,000 g of a mixed solvent composition of R225ca/R51-14=30.0%/70.0% was charged into a distillation flask, and the flask was connected to a distillation column having a number of theoretical plates of 5. Then, the composition was heated and fluxed for 2 hours. After the composition reached equilibrium, the fraction was periodically collected and analyzed by gas chromatography. The results are shown in Table 15.

EXAMPLE 35

The same procedure as in Example 34 was repeated, except that 1,000 g of a mixed solvent composition of R225ca/R51-14=75.0%/25.0% was used as a mixed solvent composition. The results as shown in Table 15.

TABLE 15

| Portion of fraction | Example 34: Composition (%) | | Example 35: Composition (%) | |
|---|---|---|---|---|
| collected (%) | R225ca | R51-14 | R225ca | R51-14 |
| 20 | 30.0 | 70.0 | 75.0 | 25.0 |
| 60 | 30.0 | 70.0 | 75.0 | 25.0 |
| 80 | 30.1 | 69.9 | 74.9 | 25.1 |

EXAMPLE 36

The same procedure as in Example 34 was repeated, except that 1,000 g of a mixed solvent composition of R225ca/R51-14/R51-14my/R51-14mcy=30.0%/50.0%/15.0%/5.0% was used as a mixed solvent composition. The results are shown in Table 16.

TABLE 16

| Portion of fraction collected | Example 36: Composition (%) | | | |
|---|---|---|---|---|
| (%) | R225ca | R51-14 | R51-14my | R51-14mcy |
| 20 | 30.0 | 50.0 | 15.0 | 5.0 |
| 60 | 30.0 | 50.0 | 15.0 | 5.0 |
| 80 | 30.1 | 49.9 | 15.0 | 5.0 |

EXAMPLE 37

The same procedure as in Example 34 was repeated, except that 1,000 g of a mixed solvent composition of R225ca/R51-14/R51-14my/R51-14mcy=75.0%/18.0%/5.0%/2.0% as a mixed solvent composition. The results are Table 17.

TABLE 17

| Portion of fraction collected | Example 37: Composition (%) | | | |
|---|---|---|---|---|
| (%) | R225ca | R51-14 | R51-14my | R51-14mcy |
| 20 | 75.0 | 18.0 | 5.0 | 2.0 |
| 60 | 75.0 | 18.0 | 5.0 | 2.0 |
| 80 | 74.9 | 18.1 | 5.0 | 2.0 |

EXAMPLE 38

250 cc of a mixed solvent composition of R225cb (b.p. 56.1° C.) and R51-14 (b.p. 56° C.) in such a ratio as shown in Table 18 was charged into an Othmer type gas-liquid equilibrium distillation apparatus, and was heated. After the composition reached equilibrium, samples were taken from the gas phase and the liquid phase and were analyzed by gas chromatography. The results are shown in Table 18. The azeotropic composition was R225cb/R51-14=45.0%/55.0%.

TABLE 18

| Example 38: Gas phase composition (%) | | Example 38: Liquid phase composition (%) | |
|---|---|---|---|
| R225cb | R51-14 | R225cb | R51-14 |
| 20.0 | 80.0 | 11.0 | 89.0 |
| 32.0 | 68.0 | 23.0 | 77.0 |
| 42.0 | 58.0 | 41.0 | 59.0 |
| 45.0 | 55.0 | 45.0 | 55.0 |
| 56.0 | 44.0 | 61.0 | 39.0 |
| 80.0 | 20.0 | 87.0 | 13.0 |

EXAMPLE 39

The same procedure as in Example 34 was repeated, except that 1,000 g of a mixed solvent composition of R225cb/R51-14=25.0%/75.0% was used as a mixed solvent composition. The results are shown in Table 19.

EXAMPLE 40

The same procedure as in Example 34 was repeated, except that 1,000 g of a mixed solvent composition of R225cb/R51-14=60.0%/40.0% was used as a mixed solvent composition. The results are shown in Table 19.

TABLE 19

| Portion of fraction collected | Example 39: Composition (%) | | Example 40: Composition (%) | |
|---|---|---|---|---|
| (%) | R225cb | R51-14 | R225cb | R51-14 |
| 20 | 25.0 | 75.0 | 60.0 | 40.0 |
| 60 | 25.0 | 75.0 | 60.0 | 40.0 |
| 80 | 25.1 | 74.9 | 59.9 | 40.1 |

EXAMPLE 41

The same procedure as in Example 34 was repeated, except that 1,000 g of a mixed solvent composition R225cb/R51-14/R51-14my/R51-14mcy=25.0%/47.0%/13.0%/5.0% as a mixed solvent composition. The results are Table 20.

TABLE 20

| Portion of fraction collected (%) | Example 41: Composition (%) | | | |
|---|---|---|---|---|
| | R225cb | R51-14 | R51-14my | R51-14mcy |
| 20 | 25.0 | 54.0 | 16.0 | 5.0 |
| 60 | 25.0 | 54.0 | 16.0 | 5.0 |
| 80 | 25.1 | 53.9 | 16.0 | 5.0 |

EXAMPLE 42

The same procedure as in Example 34 was repeated, except that 1,000 g of a mixed solvent composition of R225cb/R51-14/R51-14my/R51-14mcy=60.0%/29.0%/8.0%/3.0% as a mixed solvent composition. The results are shown in Table 21.

TABLE 21

| Portion of fraction collected (%) | Example 42: Composition (%) | | | |
|---|---|---|---|---|
| | R225cb | R51-14 | R51-14my | R51-14mcy |
| 20 | 60.0 | 29.0 | 8.0 | 3.0 |
| 60 | 60.0 | 29.0 | 8.0 | 3.0 |
| 80 | 59.9 | 29.1 | 8.0 | 3.0 |

EXAMPLE 43

The same procedure as in Example 34 was repeated, except that 1,000 g of a mixed solvent composition consisting of 50.0% of R225 of R225ca/R225cb=45/55 (weight ratio) and 50.0% of R51-14 was used as a mixed solvent composition. The results are shown in table 22.

EXAMPLE 44

The same procedure as in Example 34 was repeated, except that 1000 g of a mixed solvent composition consisting of 25.0% of R225 of R225ca/R225cb=45/55 (weight ratio) and 75.0% of R51-14 was used as a mixed solvent composition. The results are shown in table 22.

EXAMPLE 45

The same procedure as in Example 34 was repeated, except that 1,000 g of a mixed solvent composition consisting of 70.0% of R225mix of R225ca/R225cb=45/55 (weight ratio) and 30.0% of R51-14 was used as a mixed solvent composition. The results are shown in table 22.

TABLE 22

| Portion of fraction collected (%) | Example 43: Composition (%) | | Example 44: Composition (%) | | Example 45: Composition (%) | |
|---|---|---|---|---|---|---|
| | R225mix | R51-14 | R225mix | R51-14 | R225mix | R51-14 |
| 20 | 51.0 | 49.0 | 25.0 | 75.0 | 70.0 | 30.0 |
| 60 | 51.0 | 49.0 | 25.0 | 75.0 | 70.0 | 30.0 |
| 80 | 51.2 | 48.8 | 25.1 | 74.9 | 69.9 | 30.1 |

EXAMPLE 46

The same procedure as in Example 34 was repeated, except that 1,000 g of a mixed solvent composition consisting of 25.0% of R225mix of R225ca/R225cb=45/55 (weight ratio), 47.0% of R51-14, 13.0% of R51-14my and 5.0% of R51-14mcy was used as a mixed solvent composition. The results are shown in table 23.

TABLE 23

| Portion of fraction collected (%) | Example 46: Composition (%) | | | |
|---|---|---|---|---|
| | R225mix | R51-14 | R51-14my | R51-14mcy |
| 20 | 25.0 | 54.0 | 16.0 | 5.0 |
| 60 | 25.0 | 54.0 | 16.0 | 5.0 |
| 80 | 25.1 | 53.9 | 16.0 | 5.0 |

EXAMPLE 47

The same procedure as in Example 34 was repeated, except that 1,000 g of a mixed solvent composition consisting of 55.0% of R225mix of R225ca/R225cb=45/55 (weight ratio), 33.0% of R51-14, 9.0% of R51-14my and 3.0% of R51-14mcy was used as a mixed solvent composition. The results are shown in table 24.

TABLE 24

| Portion of fraction collected (%) | Example 47: Composition (%) | | | |
|---|---|---|---|---|
| | R225mix | R51-14 | R51-14my | R51-14mcy |
| 20 | 55.0 | 33.0 | 9.0 | 3.0 |
| 60 | 55.0 | 33.0 | 9.0 | 3.0 |
| 80 | 55.1 | 32.9 | 9.0 | 3.0 |

EXAMPLE 48

The same procedure as in Example 34 was repeated, except that 1,000 g of a mixed solvent composition consisting of 45.0% of R225mix of R225ca/R225cb=45/55 (weight ratio), 40.0% of R51-14, 11.0% of R51-14my and 4.0 of R51-14mcy was used as a mixed solvent ion. The results are shown in table 25.

TABLE 25

| Portion of fraction collected (%) | Example 48: Composition (%) | | | |
|---|---|---|---|---|
| | R225mix | R51-14 | R51-14my | R51-14mcy |
| 20 | 45.0 | 40.0 | 11.0 | 4.0 |
| 60 | 45.0 | 40.0 | 11.0 | 4.0 |
| 80 | 44.9 | 40.1 | 11.0 | 4.0 |

EXAMPLE 49

The same procedure as in Example 34 was repeated, except that 1,000 g of a mixed solvent composition consisting of 70.0% of R225mix of R225ca/R225cb=45/55 (weight ratio), 22.0% of R51-14, 6.0% of R51-14my and 2.0 of R51-14mcy was used as a mixed solvent on. The results are shown in table 26.

TABLE 26

| Portion of fraction collected (%) | Example 49: Composition (%) | | | |
|---|---|---|---|---|
| | R225mix | R51-14 | R51-14my | R51-14mcy |
| 20 | 70.0 | 22.0 | 6.0 | 2.0 |
| 60 | 70.0 | 22.0 | 6.0 | 2.0 |
| 80 | 69.9 | 22.1 | 6.0 | 2.0 |

EXAMPLES 50 to 60

By using the mixed solvent compositions shown in Table 27, a machine oil cleaning test (A) was carried out.

TABLE 27

| Example | Solvent Composition | % | Degree of removal A | Example | Solvent Composition | % | Degree of removal A |
|---|---|---|---|---|---|---|---|
| 50 | R225ca | 30 | ⊚ | 56 | R225cb | 45 | ⊚ |
| | R51-14 | 50 | | | R51-14 | 55 | |
| | R51-14my | 15 | | 57 | R225cb | 60 | ⊚ |
| | R51-14mcy | 5 | | | R51-14 | 29 | |
| 51 | R225ca | 40 | ⊚ | | R51-14my | 8 | |
| | R51-14 | 60 | | | R51-14mcy | 3 | |
| 52 | R225ca | 55 | ⊚ | 58 | R225ca | 10 | ⊚ |
| | R51-14 | 45 | | | R225cb | 15 | |
| 53 | R225ca | 75 | ⊚ | | R51-14 | 54 | |
| | R51-14 | 18 | | | R51-14my | 16 | |
| | R51-14my | 5 | | | R51-14mcy | 5 | |
| | R51-14mcy | 2 | | 59 | R225ca | 25 | ⊚ |
| 54 | R225cb | 25 | ⊚ | | R225cb | 25 | |
| | R51-14 | 54 | | | R51-14 | 50 | |
| | R51-14my | 16 | | 60 | R225ca | 40 | ⊚ |
| | R51-14mcy | 5 | | | R225cb | 30 | |
| 55 | R225cb | 50 | ⊚ | | R51-14 | 22 | |
| | R51-14 | 50 | | | R51-14my | 6 | |
| | | | | | R51-14mcy | 2 | |

EXAMPLES 61 to 69

By using the mixed solvent compositions shown in Table 28 and 29, defluxing test (B) and a test (C) for removing deposited water were carried out.

TABLE 28

| Example | Solvent Composition | % | Degree of removal B | Degree of removal C |
|---|---|---|---|---|
| 61 | R225ca | 25 | ⊚ | ⊚ |
| | R51-14 | 47 | | |
| | R51-14my | 13 | | |
| | R51-14mcy | 5 | | |
| | methanol | 10 | | |
| 62 | R225ca | 40 | ⊚ | ⊚ |
| | R51-14 | 50 | | |
| | ethanol | 10 | | |
| 63 | R225ca | 68 | ⊚ | ⊚ |
| | R51-14 | 20 | | |
| | R51-14my | 5 | | |
| | R51-14mcy | 2 | | |
| | 2-propanol | 5 | | |
| 64 | R225cb | 25 | ⊚ | ⊚ |
| | R51-14 | 47 | | |
| | R51-14my | 13 | | |
| | R51-14mcy | 5 | | |
| | ethanol | 10 | | |
| 65 | R225cb | 40 | ⊚ | ⊚ |
| | R51-14 | 55 | | |
| | 2-propanol | 5 | | |

TABLE 29

| Example | Solvent Composition | % | Degree of removal B | Degree of removal C |
|---|---|---|---|---|
| 66 | R225cb | 50 | ⊚ | ⊚ |
| | R51-14 | 25 | | |
| | R51-14my | 7 | | |
| | R51-14mcy | 3 | | |
| | methanol | 15 | | |
| 67 | R225ca | 10 | ⊚ | ⊚ |
| | R225cb | 45 | | |
| | R51-14 | 29 | | |
| | R51-14my | 8 | | |
| | R51-14mcy | 3 | | |
| | 2-propanol | 5 | | |
| 68 | R225ca | 20 | ⊚ | ⊚ |
| | R225cb | 20 | | |
| | R51-14 | 50 | | |
| | methanol | 10 | | |
| 69 | R225ca | 5 | ⊚ | ⊚ |
| | R225cb | 25 | | |
| | R51-14 | 40 | | |
| | R51-14my | 11 | | |
| | R51-14mcy | 4 | | |
| | ethanol | 15 | | |

EXAMPLE 70

1,000 g of a mixed solvent composition consisting of 45% of R225mix (R225ca/R225cb =45%/55%), 45% of R51-14 and 10% of methanol (MeOH) was charged into a of 5 distillation flask, and the flask was connected to a distillation column having a number of theoretical plates of 5. Then, the composition was heated and refluxed for 2 hours. After the composition reached equilibrium, the fraction was periodically collected and analyzed by gas chromatography. The results are shown in Table 30.

EXAMPLE 71

The same procedure as in Example 70 was repeated, except that 1,000 g of a mixed solvent composition consisting of 35% of R225mix (R225ca/R225cb=45%/55%), 62% of R51-14 and 3% of MeOH was used as a mixed solvent composition. The results are shown in Table 30.

TABLE 30

| Portion of fraction collected | Example 70: Composition (%) | | | Example 71: Composition (%) | | |
|---|---|---|---|---|---|---|
| (%) | R225mix | R51-14 | MeOH | R225mix | R51-14 | MeOH |
| 20 | 45.0 | 45.0 | 10.0 | 35.0 | 62.0 | 3.0 |
| 40 | 45.0 | 45.0 | 10.0 | 35.0 | 62.0 | 3.0 |
| 60 | 45.1 | 44.9 | 10.0 | 34.9 | 62.1 | 3.0 |

EXAMPLE 72

The same procedure as in Example 70 was repeated, except that 1,000 g of a mixed solvent composition consisting of 40% of R225mix (R225ca/R225cb=45%/55%), 36% of R51-14, 10% of R51-14my, 4% of R51-14mcy and 10% of MeOH was used as a mixed solvent composition. The results are shown in Table 31.

TABLE 31

| Portion of fraction collected | Example 72: Composition (%) | | | | |
|---|---|---|---|---|---|
| (%) | R225mix | R51-14 | R51-14my | R51-14mcy | MeOH |
| 20 | 40.0 | 36.0 | 10.0 | 4.0 | 10.0 |
| 40 | 40.0 | 36.0 | 10.0 | 4.0 | 10.0 |
| 60 | 39.9 | 36.1 | 10.0 | 4.0 | 10.0 |

EXAMPLE 73

The same procedure as in Example 70 was repeated, except that 1,000 g of a mixed solvent composition consisting of 50% of R225mix (R225ca/R225cb=45%/55%), 34% of R51-14, 9% of R51-14my, 4% of R51-14mcy and 3% of MeOH was used as a mixed solvent composition. The results are shown in Table 32.

TABLE 32

| Portion of fraction collected (%) | Example 73: Composition (%) | | | | |
|---|---|---|---|---|---|
| | R225mix | R51-14 | R51-14my | R51-14mcy | MeOH |
| 20 | 50.0 | 34.0 | 9.0 | 4.0 | 3.0 |
| 40 | 50.0 | 34.0 | 9.0 | 4.0 | 3.0 |
| 60 | 50.1 | 33.9 | 9.0 | 4.0 | 3.0 |

EXAMPLE 74

The same procedure as in Example 70 was repeated, except that 1,000 g of a mixed solvent composition consisting of 20% of R225mix (R225ca/R225cb=45%/55%), 75% of R51-14 and 5% of MeOH was used as a mixed solvent composition. The results are shown in Table 33.

TABLE 33

| Portion of fraction collected (%) | Example 74: Composition (%) | | |
|---|---|---|---|
| | R225mix | R51-14 | MeOH |
| 20 | 20.0 | 75.0 | 5.0 |
| 40 | 20.0 | 75.0 | 5.0 |
| 60 | 19.9 | 75.1 | 5.0 |

EXAMPLE 75

The same procedure as in Example 70 was repeated, that 1,000 g of a mixed solvent composition consisting of 45% of R225mix (R225ca/R225cb=45%/55%), 47% of R51-14 and 8% of ethanol (EtOH) was used as a mixed solvent composition. The results are shown in Table 34.

EXAMPLE 76

The same procedure as in Example 70 was repeated, that 1,000 g of a mixed solvent composition consisting of 28% of R225mix (R225ca/R225cb=45%/55%), 69% of R51-14 and 3% of EtOH was used as a mixed solvent composition. The results are shown in Table 34.

TABLE 34

| Portion of fraction collected | Example 75: Composition (%) | | | Example 76: Composition (%) | | |
|---|---|---|---|---|---|---|
| (%) | R225mix | R51-14 | EtOH | R225mix | R51-14 | EtOH |
| 20 | 45.0 | 47.0 | 8.0 | 28.0 | 69.0 | 3.0 |
| 40 | 45.0 | 47.0 | 8.0 | 28.0 | 69.0 | 3.0 |
| 60 | 45.1 | 46.9 | 8.0 | 27.9 | 69.1 | 3.0 |

The same procedures as in Example 70 was repeated, exept that 1000

EXAMPLE 77

The same procedure as in Example 70 was repeated, except that 1,000 g of a mixed solvent composition consisting of 30% of R225mix (R225ca/R225cb=45%/55%), 45% of R51-14, 12% of R51-14my, 5% of R51-14mcy and 8% of EtOH was used as a mixed solvent composition. The results are shown in Table 35.

TABLE 35

| Portion of fraction collected (%) | Example 77: Composition (%) | | | | |
|---|---|---|---|---|---|
| | R225mix | R51-14 | R51-14my | R51-14mcy | EtOH |
| 20 | 30.0 | 45.0 | 12.0 | 5.0 | 8.0 |
| 40 | 30.0 | 45.0 | 12.0 | 5.0 | 8.0 |
| 60 | 29.9 | 45.1 | 12.0 | 5.0 | 8.0 |

EXAMPLE 78

The same procedure as in Example 70 was repeated, except that 1,000 g of a mixed solvent composition consisting of 28% of R225mix (R225ca/R225cb=45%/55%), 50% of R51-14, 13% of R51-14my, 6% of R51-14mcy and 3% of EtOH was used as a mixed solvent composition. The results are shown in Table 36.

TABLE 36

| Portion of fraction collected (%) | Example 78: Composition (%) | | | |
|---|---|---|---|---|
| | R225mix | R51-14 | R51-14my | R51-14mcy | EtOH |
| 20 | 28.0 | 50.0 | 13.0 | 6.0 | 3.0 |
| 40 | 28.0 | 50.0 | 13.0 | 6.0 | 3.0 |
| 60 | 27.9 | 50.1 | 13.0 | 6.0 | 3.0 |

EXAMPLE 79

The same procedure as in Example 70 was repeated, except that 1,000 g of a mixed solvent composition consisting of 20% of R225mix (R225ca/R225cb=45%/55%), 75% of 51-14 and 5% of EtOH was used as a mixed solvent composition. The results are shown in Table 37.

TABLE 37

| Portion of fraction collected (%) | Example 79: Composition (%) | | |
|---|---|---|---|
| | R225mix | R51-14 | EtOH |
| 20 | 20.0 | 75.0 | 5.0 |
| 40 | 20.0 | 75.0 | 5.0 |
| 60 | 19.9 | 75.1 | 5.0 |

EXAMPLE 80

The same procedure as in Example 70 was repeated, except that 1,000 g of a mixed solvent composition consisting of 20% of R225mix (R225ca/R225cb=45%/55%), 73% of R51-14 and 7% of 2-propanol (2-PrOH) was used as a mixed solvent composition. The results are shown in Table 38.

EXAMPLE 81

The same procedure as in Example 70 was repeated, except that 1,000 g of a mixed solvent composition consisting of 60% of R225mix (R225ca/R225cb=45%/55%), 38.5% of R51-14 and 1.5% of 2-PrOH was used as a mixed solvent composition. The results are shown in Table 38.

TABLE 38

| Portion of fraction collected (%) | Example 80: Composition (%) | | | Example 81: Composition (%) | | |
|---|---|---|---|---|---|---|
| | R225mix | R51-14 | 2-PrOH | R225mix | R51-14 | 2-PrOH |
| 20 | 20.0 | 73.0 | 7.0 | 60.0 | 38.5 | 1.5 |
| 40 | 20.0 | 73.0 | 7.0 | 60.0 | 38.5 | 1.5 |
| 60 | 20.1 | 72.9 | 7.0 | 59.9 | 38.6 | 1.5 |

EXAMPLE 82

The same procedure as in Example 70 was repeated, except that 1,000 g of a mixed solvent composition consisting of 30% of R225mix (R225ca/R225cb=45%/55%), 46% of R51-14, 12% of R51-14my, 5% of R51-14mcy and 7% of 2-PrOH was used as a mixed solvent composition. The results are shown in Table 39.

TABLE 39

| Portion of fraction collected (%) | Example 82: Composition (%) | | | | |
|---|---|---|---|---|---|
| | R225mix | R51-14 | R51-14my | R51-14mcy | 2-PrOH |
| 20 | 30.0 | 46.0 | 12.0 | 5.0 | 7.0 |
| 40 | 30.0 | 46.0 | 12.0 | 5.0 | 7.0 |
| 60 | 29.9 | 46.1 | 12.0 | 5.0 | 7.0 |

EXAMPLE 83

The same procedure as in Example 70 was repeated, except that 1,000 g of a mixed solvent composition consisting of 50% of R225mix (R225ca/R225cb=45%/55%), 35% of R51-14, 9% of R51-14my, 4.5% of R51-14mcy and 1.5% of 2-PrOH was used as a mixed solvent composition. The are shown in Table 40.

TABLE 40

| Portion of fraction collected (%) | Example 83: Composition (%) | | | | |
|---|---|---|---|---|---|
| | R225mix | R51-14 | R51-14my | R51-14mcy | 2-PrOH |
| 20 | 50.0 | 35.0 | 9.0 | 4.5 | 1.5 |
| 40 | 50.0 | 35.0 | 9.0 | 4.5 | 1.5 |
| 60 | 50.1 | 34.9 | 9.0 | 4.5 | 1.5 |

EXAMPLE 84

The same procedure as in Example 70 was repeated, except that 1,000 g of a mixed solvent composition consisting of 20% of R225mix (R225ca/R225cb=45%/55%), 75% of R51-14 and 5% of 2-PrOH was used as a mixed composition. The results are shown in Table 41.

TABLE 41

| Portion of fraction collected (%) | Example 84: Composition (%) | | |
|---|---|---|---|
| | R225mix | R51-14 | 2-PrOH |
| 20 | 20.0 | 75.0 | 5.0 |
| 40 | 20.0 | 75.0 | 5.0 |
| 60 | 20.1 | 74.9 | 5.0 |

EXAMPLES 85 to 98

By using the mixed solvent compositions shown in Table 42 (R225mix is a mixture of R225ca/R225cb=45%/55%), a machine oil cleaning test (A), a defluxing test (B) and a test (C) for removing deposited water were carried out. In Table 42, A, B and C indicate the degrees of removal A, B and C of the respective tests.

TABLE 42

| Example | Solvent composition | % | A | B | C |
|---|---|---|---|---|---|
| 85 | R225mix/R51-14/MeOH | 45/45/10 | ⊙ | ⊙ | ⊙ |
| 86 | R225mix/R51-14/MeOH | 35/62/3 | ⊙ | ⊙ | ⊙ |
| 87 | R225mix/R51-14/R51-14my/R51-14mcy/MeOH | 40/36/10/4/10 | ⊙ | ⊙ | ⊙ |
| 88 | R225mix/R51-14/R51-14my/R51-14mcy/MeOH | 50/34/9/4/3 | ⊙ | ⊙ | ⊙ |
| 89 | R225mix/R51-14/EtOH | 45/47/8 | ⊙ | ⊙ | ⊙ |

TABLE 42-continued

| Example | Solvent composition | % | A | B | C |
|---|---|---|---|---|---|
| 90 | R225mix/R51-14/EtOH | 28/69/3 | ◎ | ◎ | ◎ |
| 91 | R225mix/R51-14/R51-14my/R51-14mcy/EtOH | 30/45/12/5/8 | ◎ | ◎ | ◎ |
| 92 | R225mix/R51-14/R51-14my/R51-14mcy/EtOH | 28/50/13/6/3 | ◎ | ◎ | ◎ |
| 93 | R225mix/R51-14/R51-14my/R51-14mcy/EtOH/2-PrOH | 30/45/12/5/6/2 | ◎ | ◎ | ◎ |
| 94 | R225mix/R51-14/R51-14my/R51-14mcy/EtOH/MeOH | 30/45/12/5/6/2 | ◎ | ◎ | ◎ |
| 95 | R225mix/R51-14/2-PrOH | 20/73/7 | ◎ | ◎ | ◎ |
| 96 | R225mix/R51-14/2-PrOH | 66/38.5/1.5 | ◎ | ◎ | ◎ |
| 97 | R225mix/R51-14/R51-14my/R51-14mcy/2-PrOH | 30/46/12/5/7 | ◎ | ◎ | ◎ |
| 98 | R225mix/R51-14/R51-14my/R51-14mcy/2-PrOH | 50/35/9/4.5/1.5 | ◎ | ◎ | ◎ |

We claim:

1. A mixed solvent composition, which consists essentially of dichloropentafluoropropane and 1,1,1,2,3,4,4,5,5,5,-decafluoropentane as essential components.

2. The mixed solvent composition of claim 1, wherein the proportion of 1,1,1,2,2,3,4,4,5,5,5-decafluoropentane is from 10 to 1000 parts by weight to 100 parts by weight of dichloropentafluoropropane.

3. The mixed solvent composition of claim 1, which is a mixture comprising from 10 to 50% by weight of an isomer mixture of diclohropentafluoropropane and from 50 to 90% by weight of 1,1,1,2,3,4,4,5,5,5-decafluoropentane, wherein said mixed solvent composition varies only within a range of ±2% with repeated distillation-condensation.

4. The mixed solvent composition of claim 3, wherein the isomer mixture of the dichloropentafluoropropane consists essentially from 1 to 99% by weight of 3,3-dichloro-1,1,1,2,2-pentafluoropropane and from 1 to 99% by weight of 1,3-dichloro-1,1,2,2,3-pentafluoropropane.

5. A mixed solvent composition, which is a mixture comprising from 45 to 60% by weight of 3,3-dichloro-1,1,1,2,2-pentafluoropropane and from 40 to 55% by weight of 1,1,1,2,3,4,4,5,5-decayluoropentane, and wherein said mixed solvent composition varies only within a range of ±2% with repeated distillation-condensation.

6. A mixed solvent composition, which is mixture comprising from 30 to 50% by weight of 1,3-dichloro-1,1,2,2,3-pentafluoropropane and from 50 to 70% by weight 1,1,1,2,3,4,4,5,5,5-decafluoropentane, and wherein said mixed solvent composition varies only within a range of ±2% with repeated distillation-condensation.

* * * * *

UNITED STATES PATENT AND TRADEMARK OFFICE
CERTIFICATE OF CORRECTION

PATENT NO.    : 6,042,749                         Page 1 of 1
DATED         : March 28, 2000
INVENTOR(S)   : Kenroh Kitamura et al.

It is certified that error appears in the above-identified patent and that said Letters Patent is hereby corrected as shown below:

Title page, item [63],
The Related U.S. Application Data, the PCT information has been omitted. It should read as follows:

-- Related U.S. Application Data

[63] Continuation of application No. 08/578,533, Jan. 18, 1996, Pat. No. 5,827,454, which is a 371 of PCT/JP95/00948, May 18, 1995. --

Column 1,
The Related U.S. Application Data is incorrectly listed. It should read as follows:

-- This application is a Continuation of application No. 08/578,533, filed on Jan. 18, 1996, now U.S. Pat. No. 5,827,454, which was filed as International Application PCT/JP95/00948, filed May 18, 1995. --

Signed and Sealed this

Twenty-first Day of August, 2001

*Attest:*

*Attesting Officer*

NICHOLAS P. GODICI
*Acting Director of the United States Patent and Trademark Office*